US010537915B2

(12) United States Patent
Park et al.

(10) Patent No.: US 10,537,915 B2
(45) Date of Patent: Jan. 21, 2020

(54) CONTAMINANT RESISTANT COATING FABRICATION STRUCTURE AND METHOD (75) Inventors: Shawn Park, Cerritos, CA (US); John Belk, St. Louis, MO (US)

(73) Assignee: The Boeing Company, Chicago, IL (US)

( * ) Notice: Subject to any disclaimer, the term of this patent is extended or adjusted under 35 U.S.C. 154(b) by 906 days.

(21) Appl. No.: 12/609,352

(22) Filed: Oct. 30, 2009

(65) Prior Publication Data
US 2010/0316844 A1 Dec. 16, 2010

Related U.S. Application Data (63) Continuation-in-part of application No. 12/211,030, filed on Sep. 15, 2008, now Pat. No. 10,188,103.

(51) Int. Cl.
B05D 5/08 (2006.01)
A01N 61/00 (2006.01)
A01N 25/34 (2006.01)
B08B 17/06 (2006.01)

(52) U.S. Cl.
CPC .............. B05D 5/08 (2013.01); A01N 25/34 (2013.01); A01N 61/00 (2013.01); Y10T 428/24612 (2015.01); Y10T 428/31504 (2015.04)

(58) Field of Classification Search
CPC .......... A01N 25/34; A01N 61/00; B05D 5/08; A61K 9/0021; A61K 9/7038
See application file for complete search history.

(56) References Cited

U.S. PATENT DOCUMENTS

| | | | |
|---|---|---|---|
| 3,755,713 A | 8/1973 | Paszkowski | |
| 4,502,092 A | 2/1985 | Bannink, Jr. et al. | |
| 4,912,594 A | 3/1990 | Bannink, Jr. et al. | |
| 5,490,962 A | 2/1996 | Cima et al. | |
| 5,538,732 A | 7/1996 | Smith et al. | |
| 6,068,911 A | 5/2000 | Shouji et al. | |
| 6,723,428 B1 | 4/2004 | Foss et al. | |
| 6,986,853 B2 | 1/2006 | Glatkowski et al. | |
| 7,307,825 B2 | 12/2007 | De La Fuente De Ana et al. | |
| 7,364,756 B2 | 4/2008 | Gabbay | |
| 7,935,214 B2 | 5/2011 | Gammon et al. | |
| 8,057,888 B2 | 11/2011 | Gammon et al. | |
| 8,512,507 B2 | 8/2013 | Gammon et al. | |
| 10,188,103 B2 | 1/2019 | Peltz et al. | |
| 2003/0091767 A1 | 5/2003 | Podhajny | |
| 2003/0113520 A1 | 6/2003 | Takahashi et al. | |
| 2003/0170453 A1 | 9/2003 | Foss et al. | |
| 2004/0115167 A1* | 6/2004 | Cormier et al. | 424/85.1 |
| 2004/0156918 A1 | 8/2004 | Podhajny | |
| 2005/0203237 A1* | 9/2005 | Dekkers et al. | 524/450 |
| 2005/0208275 A1* | 9/2005 | Abe et al. | 428/195.1 |
| 2005/0228477 A1* | 10/2005 | Grainger et al. | 623/1.11 |
| 2006/0024508 A1* | 2/2006 | D'Urso et al. | 428/426 |
| 2006/0035039 A1 | 2/2006 | Ylitalo et al. | |
| 2006/0153993 A1 | 7/2006 | Schmidt et al. | |
| 2006/0292208 A1 | 12/2006 | Vachon | |
| 2007/0227428 A1* | 10/2007 | Brennan et al. | 114/67 R |
| 2007/0232166 A1 | 10/2007 | Hayashi et al. | |
| 2007/0292486 A1 | 12/2007 | Sen et al. | |
| 2008/0145528 A1 | 6/2008 | Deng et al. | |
| 2010/0316844 A1 | 12/2010 | Park et al. | |

FOREIGN PATENT DOCUMENTS

| | | |
|---|---|---|
| CA | 2095312 | 11/1993 |
| DE | 10014486 | 10/2001 |
| EP | 0568322 | 11/1993 |
| EP | 0633327 | 1/1995 |
| EP | 0719594 | 7/1996 |
| EP | 2168432 | 3/2010 |
| EP | 2319632 | 5/2011 |
| JP | S57137549 | 8/1982 |
| JP | H11300921 | 2/1999 |
| JP | 2001096674 | 4/2001 |
| JP | 2001152051 | 6/2001 |
| JP | 2003211569 | 7/2003 |
| JP | 2003213397 | 7/2003 |
| JP | 2005205378 | 8/2005 |
| JP | 2007270378 | 10/2007 |
| JP | 2007289873 | 11/2007 |
| JP | 2008180003 | 8/2008 |
| JP | 2008183482 | 8/2008 |
| JP | 2008-238440 | * 10/2008 |
| JP | 2008265236 | 11/2008 |
| WO | 0041530 | 7/2000 |
| WO | 03039766 | 5/2003 |
| WO | 2004030743 | 4/2004 |

(Continued)

OTHER PUBLICATIONS

Machine translation of JP 2008-238440 published Oct. 2008, p. 1-16.*
Schumacher, et al, "Engineered nanoforce gradients for inhibition of settlement (attachment) of swimming algal spores," American Chemical Society, Mar. 25, 2008, [http://www.researchgate.net/publication/5489925_Engineered_nanoforce_gradients_for_inhibition_of_settlement_%28attachment%29_of_swimming_algal_spores], retrieved on Jul. 14, 2015, 8 pages.
Hoowaki, "Hookwaki Technology," [http://www.hoowaki.com/], retrieved on Jul. 15, 2015, 1 page.
John Bohannon, "'Smart Coatings' Research Shows the Virtues of Superficiality," Science Magazine, vol. 309, Jul. 15, 2005, [http://www.johnbohannon.org/NewFiles/nanocoatings.pdf], retrieved on Jul. 15, 2015, 2 pages.
Cannon et al., "Hydrophobicity of curved microstructured surfaces," Journal of Micromechanics and Microengineering, vol. 20, Jan. 18, 2010, [http://www.hoowaki.com/files/research/2010-jmm-hydrophobic-curved.pdf], retrieved on Jul. 15, 2015, 6 pages.

(Continued)

Primary Examiner — Bethany P Barham
Assistant Examiner — Peter Anthopolos
(74) Attorney, Agent, or Firm — Hanley, Flight & Zimmerman, LLC (57) ABSTRACT An illustrative embodiment of a contaminant resistant structure includes a substrate having a substrate surface, at least one contaminant resistant material provided on the substrate surface and a hydrophobic or oleophobic, and alternatively, a hydrophilic or oleophilic material provided on at least a portion of the substrate surface.

13 Claims, 8 Drawing Sheets (56) References Cited

FOREIGN PATENT DOCUMENTS

| WO | 2005014742 | 2/2005 |
|---|---|---|
| WO | 2007147094 | 12/2007 |

OTHER PUBLICATIONS

Cannon et al., "Visualizing contact line phenomena on microstructured superhydrophobic surfaces," Journal of Vacuum Science and Technology, vol. 28 (3), May 2010, [http://www.hoowaki.com/files/research/2010-jvst-droplet.pdf], retrieved on Jul. 15, 2015, 4 pages.
United States Patent and Trademark Office, "Decision on Appeal," issued in connection with U.S. Appl. No. 12/211,030, dated Dec. 19, 2017, 7 pages.
European Patent Office, "Communication Pursuant to Article 94(3) EPC," issued in connection with European Patent Application No. 09170242,3, dated Aug. 4, 2016, 3 pages.
European Patent Office, "Communication Under Rule 71(3) EPC," issued in connection with European Patent Application No. 09170242. 3, dated May 2, 2017, 60 pages.
Gardiner, "Lightning Strike Protection for Composite Structures," High Performance Composites, Jul. 1, 2006, [http://www.compositesworld.com/articles/lightning-strike-protection-for-composite-structures], retrieved on Jun. 24, 2015, 8 pages.
Schumacher, James F. et al., "Species-Specific Engineered Antifouling Topographies: Correlations Between the Settlement of Algal Zoospores and Barnacle Cybrids," Biofouling, 2007, 23(5): 307-317.
Schumacher, James F. et al., "Engineered Antifouling Microtopographies—Effect of Feature Size, Geometry, and Roughness on Settlement of Zoospores of the Green Alga Ulva," Biofouling, 2007, 23(1): 55-62.
Feinberg, Adam W. et al., "Systematic Variation of Microtopography, Surface Chemistry and Elastic Modulus and the State Dependent Effect on Endothelial Cell Alignment," Wiley InterScience (www.interscience.wiley.com) DOI: 10.1002/jbm.a.31626, Nov. 9, 2007, 13 pages.
United States Patent and Trademark Office, "Examiner's Answer to Appeal Brief," issued in connection with U.S. Appl. No. 12/211,030, dated Jul. 7, 2016, 13 pages.
United States Patent and Trademark Office, "Final Office Action," issued in connection with U.S. Appl. No. 12/211,030, dated Jun. 29, 2015, 11 pages.
United States Patent and Trademark Office, "Non-final Office Action," issued in connection with U.S. Appl. No. 12/211,030, dated Nov. 14, 2014, 35 pages.
United States Patent and Trademark Office, "Final Office Action," issued in connection with U.S. Appl. No. 12/211,030, dated Jan. 25, 2012, 16 pages.
United States Patent and Trademark Office, "Non-final Office Action," issued in connection with U.S. Appl. No. 12/211,030, dated Aug. 23, 2011, 17 pages.
European Patent Office, "Extended Search Report," issued in connection with European Patent Application No. 10188345.2, dated Jan. 28, 2011, 9 pages.
Cho et al., "Methods for Distributed Design and Fabrication of Parts with Local Composition Control," Proceedings of the 2001 NSF Design and Manufacturing Grantees Conference, 2001, 15 pages.
Kosanovic et al., "Mechanochernisty of Zeolites: Part 2. Change in Particulate Properties of Zeolites During Ball Milling," Zeolites, vol. 15, pp. 247-252 (1995), 11 pages.
European Patent Office, "Extended Search Report," issued in connection with European Patent Application No. 09170242.3, dated Feb. 26, 2010, 5 pages.
United States Patent and Trademark Office, "Notice of Allowance," issued in connection with U.S. Appl. No. 12/211,030, dated Mar. 2, 2018, 9 pages.
United States Patent and Trademark Office, "Advisory Action," issued in connection with U.S. Appl. No. 12/211,030, dated Oct. 22, 2015, 12 pages.
Japanese Patent Office, "Search Report by Registered Searching Organization," issued in connection with Japanese Patent Application No. 2009-211168, dated May 22, 2013, 18 pages (includes english translation).
Japanese Patent Office, "Notification of Reasons for Refusal," issued in connection with Japanese Patent Application No. 2009-211168, dated May 28, 2013, 6 pages (includes English translation).
Japanese Patent Office, "Notification of Reasons for Refusal," issued in connection with Japanese Patent Application No. 2009-211168, dated Jun. 12, 2014, 8 pages (includes English translation).
Japanese Patent Office, "Decision to Grant a Patent," issued in connection with Japanese Patent Application No. 2009-211168, dated Apr. 27, 2015, 6 pages (includes English translation).
Japanese Patent Office, "Search Report by Registered Searching Organization," issued in connection with Japanese Patent Application No. 2010-243051, dated Jul. 17, 2014, 11 pages (includes English translation).
Japanese Patent Office, "Notification of Reasons for Refusal," issued in connection with Japanese Patent Application No. 2010-243051, dated Jul. 25, 2014, 6 pages (includes English translation).
Japanese Patent Office, "Decision to Grant a Patent," issued in connection with Japanese Patent Application No. 2010-243051, dated Feb. 16, 2015, 5 pages (includes English translation).
European Patent Office, "Communication Pursuant to Article 94(3) EPC," issued in connection with European Patent Application No. 10188345.2, dated Nov. 7, 2017, 8 pages.
United States Patent and Trademark Office, "Notice of Allowance," issued in connection with U.S. Appl. No. 12/211,030, dated Sep. 20, 2018, 18 pages.
Canadian Patent Office, "Office Action," issued in connection with Canadian Application No. 2,678,388, dated Sep. 11, 2013, 3 pages.
Canadian Patent Office, "Office Action," issued in connection with Canadian Application No. 2,678,388, dated Jun. 5, 2014, 2 pages.
Canadian Patent Office, "Office Action," issued in connection with Canadian Application No. 2,867,737, dated Aug. 24, 2015, 3 pages.
Canadian Patent Office, "Office Action," issued in connection with Canadian Application No. 2,714,589, dated Nov. 28, 2013, 3 pages.
Canadian Patent Office, "Office Action," issued in connection with Canadian Application No. 2,714,589, dated Jun. 3, 2014, 2 pages.

* cited by examiner

CONTAMINANT RESISTANT COATING FABRICATION STRUCTURE AND METHOD

CROSS-REFERENCE TO RELATED APPLICATIONS

This application is a Continuation-In-Part application of, and claims the benefit of U.S. application Ser. No. 12/211,030, filed Sep. 15, 2008 now U.S. Pat. No. 10,188,103 entitled "ANTIMICROBIAL COATING FABRICATION METHOD AND STRUCTURE" which is incorporated here by reference in its entirety.

TECHNICAL FIELD

The disclosure relates to materials and structures having antimicrobial, antiviral, antifungal, biocidal and/or antichemical properties and methods of fabricating antimicrobial, antiviral, antifungal, biocidal and/or antichemical surface coatings. More particularly, the disclosure relates to an antimicrobial, antiviral, antifungal, biocidal and/or antichemical coating fabrication method and structure in which a coating may be applied to a surface in such a manner that different antimicrobial, antiviral, antifungal, biocidal and/or antichemical materials in the coating may remain unmixed to substantially retain or optimize the full efficacy of the materials.

BACKGROUND

Various antimicrobial, antiviral, antifungal, biocidal and/or antichemical (hereinafter contaminant resistant) materials and coatings are known. In fabrication of a contaminant resistant plastic product, a single biocide may be added to a plastic resin which may then be blended, melted and molded or extruded into the final product. In fabrication of a fabric having contaminant resistant properties, a single biocide (which may be a well-known biocide or a biocide which is currently in research, such as a fullerene, for example and without limitation), may be added to a fabric substrate by foaming, padding, spraying or dipping. In fabrication of ionic contaminant resistant agents (such as silver ions, for example), the ions may be embedded in a zeolite structure. Recent developments in nanotechnology have enabled embedding of silver ions in various materials such as fabric and plastic, for example. During the preparation process, silver nanoparticles may be immobilized on fibers using the layer-by-layer deposition method. This step may involve dipping or treatment of the fibers in various solutions.

The contaminant resistant efficacy of a contaminant resistant coating may be limited by the use of a single type of contaminant resistant material in the coating. Moreover, the mixing of various contaminant resistant agents in a resin may neutralize or precipitate the agents, possibly resulting in a less potent contaminant resistant coating or structure than would be attained using a single contaminant resistant agent. Combination of multiple types of contaminant resistant materials in a selected pattern on a surface of a structure or in a coating, and optimization of the three-dimensional parameters of the pattern, may optimize the contaminant resistant efficacy of the contaminant resistant materials.

Therefore, a contaminant resistant coating deposition method and structure is needed in which the three-dimensional parameters of a pattern of contaminant resistant materials in a coating may be controlled at multiple scales of dimension to optimize the contaminant resistant efficacy of two or more of the contaminant resistant materials in the coating.

SUMMARY

The disclosure is generally directed to a contaminant resistant structure. An illustrative embodiment of the contaminant resistant structure includes a substrate having a substrate surface, at least one contaminant resistant material provided on the substrate surface and a hydrophobic or oleophobic material provided on at least a portion of said substrate surface. One example of an oleophobic material is a material that is human body oil resistant.

The disclosure is further generally directed to a contaminant resistant structure. An illustrative embodiment of the contaminant resistant structure includes a substrate having a three-dimensional substrate surface including a plurality of elevated surfaces and a hydrophilic or oleophilic material provided on each of the plurality of elevated surfaces. By three-dimensional substrate surface, it is meant a substrate surface that has peaks of at least 3 micron in height. The three-dimensional substrate surface can be formed by a variety of well known techniques. While a substrate surface that has peaks of less than 3 micron in height is a two dimensional substrate surface in the context of this disclosure.

The disclosure is further generally directed to a method of fabricating a contaminant resistant structure. An illustrative embodiment of the method includes providing a substrate, providing at least one contaminant resistant material on the substrate and providing a hydrophobic or oleophobic material on at least a portion of the substrate.

In some embodiments, a method of fabricating a contaminant resistant structure may include providing a substrate; providing three-dimensional structures comprising a plurality of elevated surfaces on the substrate; and providing a hydrophilic or oleophilic material on the elevated surfaces.

In some embodiments, a contaminant resistant structure may include a substrate having a three-dimensional substrate surface including a plurality of elevated surfaces and a plurality of generally planar depressed surfaces extending between said elevated surfaces. Each of the elevated surfaces may include a top surface portion and a side surface portion extending from the top surface portion to the depressed surfaces. At least one contaminant resistant material may be provided on the depressed surfaces. A hydrophobic or oleophobic material may be provided on the top surface portion and the side surface portion of each of the elevated surfaces.

In some embodiments, the contaminant resistant structure may include a substrate having a three-dimensional substrate surface including a plurality of elevated surfaces and a plurality of generally planar depressed surfaces extending between the elevated surfaces. Each of the elevated surfaces may include a top surface portion and a side surface portion extending from the top surface portion to the depressed surfaces. A hydrophilic or oleophilic material may be provided on the top surface portion and the side surface portion of each of the elevated surfaces.

In some embodiments, a method of fabricating a contaminant resistant structure may include providing a substrate having a substrate surface and providing a plurality of three-dimensional structures having a plurality of elevated surfaces and a plurality of generally planar depressed surfaces extending between the elevated surfaces in the substrate surface. Each of the elevated surfaces may include a top surface portion and a side surface portion extending from the top surface portion to the depressed surfaces. A contaminant resistant material may be provided on the depressed surfaces. A hydrophobic or oleophobic material may be provided on the top surface portion and the side surface portions of each of the elevated surfaces.

In some embodiments, the method of fabricating a contaminant resistant structure may include providing a substrate having a substrate surface and providing a plurality of three-dimensional structures including plurality of elevated surfaces and a plurality of generally planar depressed surfaces extending between the elevated surfaces in the substrate surface. Each of the elevated surfaces may include a top surface portion and a side surface portion extending from the top surface portion to the depressed surfaces. A hydrophilic or oleophilic material may be provided on the top surface portion and the side surface portions of each of the elevated surfaces.

BRIEF DESCRIPTION OF THE ILLUSTRATIONS

DETAILED DESCRIPTION

The disclosure is generally directed to a method of fabricating an antimicrobial, antiviral, antifungal, biocidal and/or antichemical (hereinafter contaminant resistant) surface coating. As used herein, "contaminant" includes microbial, viral, fungal, biological and/or chemical contaminant, for example and without limitation. In some embodiments the method may include, for example and without limitation, providing at least first and second coating applicator media; providing at least first and second contaminant resistant materials; adding the first contaminant resistant material (such as $TiO_2$, Ag, fullerences and/or $H_2O_2$, for example and without limitation) to the first coating applicator medium and the second contaminant resistant material to the second coating applicator medium; providing a substrate having a surface; applying the first coating applicator medium with the first contaminant resistant material to the surface of the substrate; applying the second coating applicator medium with the second contaminant resistant material to the surface of the substrate with the second contaminant resistant material adjacent to the first contaminant resistant material; and curing the first and second coating applicator media. In some embodiments the first coating applicator medium, the second coating applicator medium and any additional coating applicator medium may be successively applied to the surface of the substrate using any suitable three-dimensional printing technique which is known to those skilled in the art to disperse or distribute the first, second and any additional contaminant resistant material in a multi-layered, three-dimensional pattern in the contaminant resistant surface coating. In some embodiments, the three-dimensional printing technique which is used to apply the first and second and any additional coating applicator media to the surface of the substrate may include ink jet printing or screen printing, for example and without limitation.

The disclosure is further generally directed to a contaminant resistant structure which may include a contaminant resistant coating applied to a surface as a pattern (which may be a random distribution, an organized distribution or both a random distribution and an organized distribution) in which different contaminant resistant materials remain substantially unmixed to retain or optimize the full contaminant resistant efficacy of the materials. The three-dimensional geometric parameters of the pattern of contaminant resistant materials in the structure or coating may be controlled at multiple scales of magnitude to optimize the contaminant resistant efficacy of the contaminant resistant materials. Accordingly, the various contaminant resistant materials may be dispersed in substantially adjacent relationship with respect to each other in the pattern at spacings which may vary from microns to one millimeter, for example and without limitation, optimizing the contaminant resistant efficacy of the coating. The contaminant resistant materials may be applied separately and successively in a layer-by-layer pattern to the surface to substantially maintain separation of the materials from each other in the pattern. In some embodiments, the first coating applicator medium and the second coating applicator medium may be applied to the surface of the substrate using any suitable three-dimensional printing technique which is known to those skilled in the art. In some embodiments, the contaminant resistant materials may be applied to the substrate surface using ink jet printing, for example and without limitation.

Figure 1:
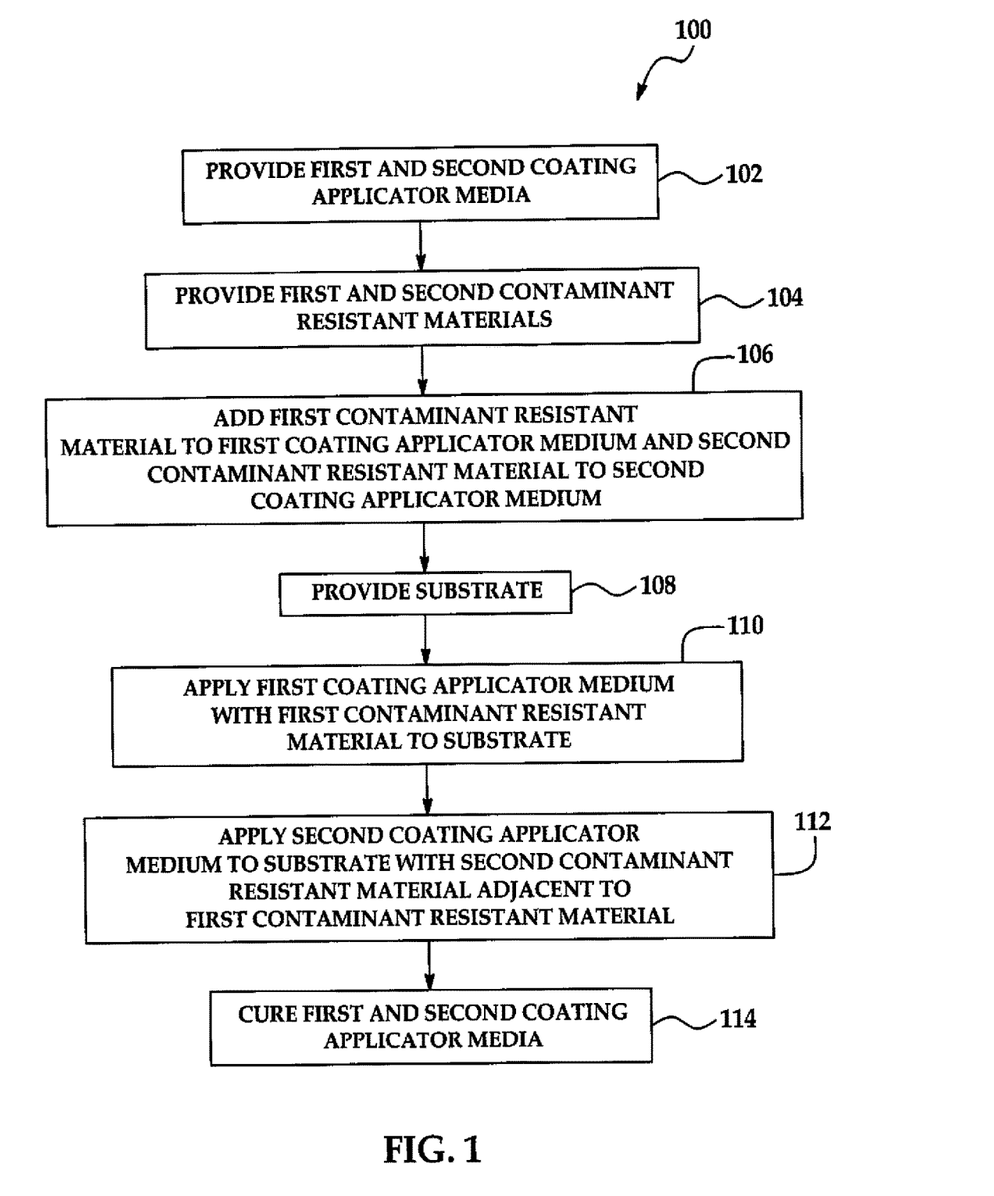
FIG. 1 is a flow diagram of an illustrative embodiment of a method of fabricating a contaminant resistant surface coating.

Referring initially to FIG. 1, a flow diagram 100 of an illustrative embodiment of a method of fabricating a contaminant resistant surface coating is shown. In block 102, first and second coating applicator media may be provided. Each of the first and second coating applicator media may include any type of medium which is suitable for applying contaminant resistant materials to a surface of a substrate. The first and second coating applicator media may include, for example and without limitation, applicator paint. In some applications, additional coating applicator media may be provided depending on the number of different types of contaminant resistant materials which are to be applied to the surface of the substrate.

In block 104, first and second contaminant resistant materials of different types may be provided. Each of the first and second contaminant resistant materials may be any type of material which is capable of killing microorganisms such as bacteria or fungi, for example and without limitation, and/or destroying or inactivating viruses and/or other microorganisms. In some applications, each of the first and second contaminant resistant material may include a biocide (which may be a well-known biocide or a biocide which is currently in research, such as a fullerance), for example and without limitation. In some applications, additional contaminant resistant materials may be provided in addition to the first and second contaminant resistant materials. The contaminant resistant materials may be selected depending on the target range of microorganisms against which contaminant resistant action is desired.

In block 106, the first contaminant resistant material may be added to the first coating applicator medium and the second contaminant resistant material may be added to the second coating applicator medium. In some applications, additional contaminant resistant materials may be added to additional coating applicator media, respectively. In some applications, two or more contaminant resistant materials may be added to each coating application medium.

In block 108, a substrate having a substrate surface may be provided. The substrate may be any desired material the substrate surface of which is to have contaminant resistant properties, including but not limited to plastic; metal; wood; glass; or fabric.

In block 110, the first coating applicator medium with the first contaminant resistant material may be applied to the surface of the substrate. In block 112, the second coating applicator medium may subsequently be applied to the surface of the substrate with the second contaminant resistant material adjacent to the first contaminant resistant material. Additional coating applicator media, each having a selected type of contaminant resistant material, may be subsequently applied to the surface of the substrate in successive layers. In some applications, each of the first coating applicator medium and the second coating applicator medium may include two or more contaminant resistant materials.

The first coating applicator medium, the second coating applicator medium and any additional coating applicator media may each be applied to the surface of the substrate using any suitable three-dimensional deposition technique which is known to those skilled in the art. Deposition of the coating applicator medium to the substrate may include, for example and without limitation, application by micro-jets; micro-nozzles; micro-dispensers; electrostatic deposition; screen printing; patterned absorption using factors that enhance adherence; or using bio-organisms as carriers. In some applications, the coating applicator media may be applied to the surface of the substrate using an ink jet printing technique, for example and without limitation. The applied coating applicator media with contaminant resistant materials may form a multilayered contaminant resistant coating on the surface of the substrate. In the contaminant resistant coating, the contaminant resistant materials of different types may form a three-dimensional pattern in which the contaminant resistant materials may be disposed in substantially adjacent and overlapping relationship with respect to each other. In some applications, the contaminant resistant materials of different types in the successive layers of the contaminant resistant coating may be separated from each other by a spacing of from about 1 micron to about 1 millimeter, for example and without limitation, in the pattern. In block 114, the first, second and any subsequent coating applicator media may be cured. In some applications, two or more contaminant resistant materials of different types may be provided in each layer of the contaminant resistant coating. The contaminant resistant materials in each layer may form separate overlapping, staggered or adjacent patterns.

Figure 2:
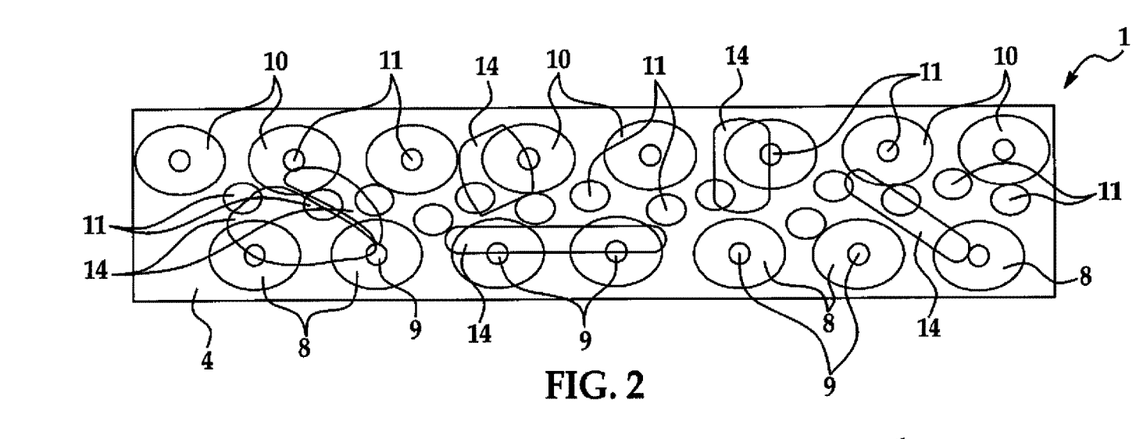
FIG. 2 is a top view of an illustrative embodiment of the contaminant resistant structure in which contaminant resistant materials are applied to a surface of a substrate in a coating according to geometrical parameters which optimize the contaminant resistant efficacy of the materials.
Figure 3:
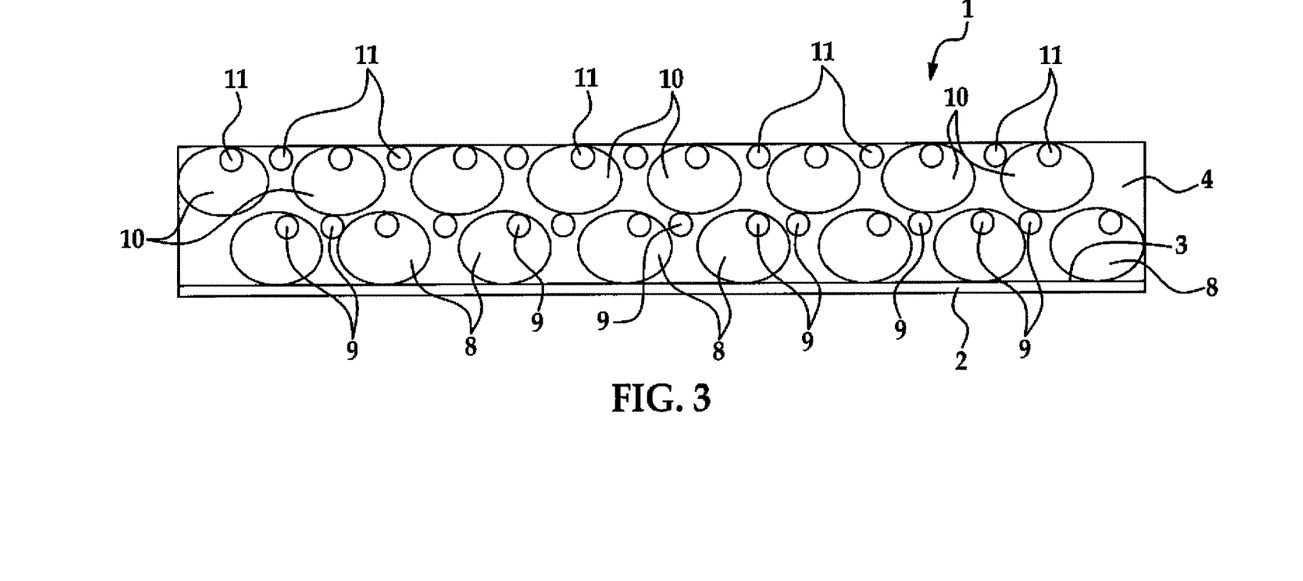
FIG. 3 is a side view of an illustrative embodiment of the contaminant resistant structure shown in FIG. 2.

Referring next to FIGS. 2 and 3, an illustrative embodiment of a contaminant resistant structure is generally indicated by reference numeral 1 in top and side views, respectively. The contaminant resistant structure 1 may include a substrate 2 (FIG. 3) having a substrate surface 3. The substrate 2 may be any desired material the substrate surface 3 of which is to have contaminant resistant properties, including but not limited to plastic; metal; wood; glass; or fabric.

A contaminant resistant coating 4 may be provided on the substrate surface 3 of the substrate 2. At least two different types of contaminant resistant material may be provided in the contaminant resistant coating 4. In the embodiment of the contaminant resistant structure 1 which is shown in FIGS. 2 and 3, a first contaminant resistant material 8; a second contaminant resistant material 9; a third contaminant resistant material 10; and a fourth contaminant resistant material 11 may be provided in the contaminant resistant coating 4. However, in some embodiments the contaminant resistant coating 4 may include more than four different types of contaminant resistant material depending on the desired range of microorganisms which is to be targeted by the contaminant resistant coating 4.

The contaminant resistant coating 4 may be applied to the substrate surface 3 in a multi-layered manner as two or more successively-applied coating applicator media, each of which may include at least one selected type of contaminant resistant material. Each layer of coating applicator media may include any type of medium which is suitable for applying contaminant resistant materials to the substrate surface 3 of the substrate 2. Each layer of coating applicator media may include, for example and without limitation, applicator paint.

As shown in FIGS. 2 and 3, in some embodiments the layers of coating applicator media may be successively deposited on the substrate surface 3 (FIG. 3) in a three-dimensional pattern in which the first contaminant resistant material 8 may be disposed generally adjacent to the substrate surface 3 of the substrate 2; the second contaminant resistant material 9 may be disposed generally adjacent to the first contaminant resistant material 8; the third contaminant resistant material 10 may be disposed generally adjacent to the second contaminant resistant material 9; and the fourth contaminant resistant material 11 may be disposed generally adjacent to the third contaminant resistant material 10. The contaminant resistant materials 8, 9, 10 and 11 may be disposed in staggered or overlapping relationship with respect to each other when viewed from above as shown in FIG. 2 and when viewed from the side as shown in FIG. 3. In some embodiments, at least two contaminant resistant materials of different type, such as the first contaminant resistant material 8 and the second contaminant resistant material 9, may be disposed together in a first layer, and at least two contaminant resistant materials of different type, such as the third contaminant resistant material 10 and the fourth contaminant resistant material 11, may be disposed together in a second layer, on the substrate surface 3.

In some embodiments, the adjacent contaminant resistant materials 8, 9, 10, 11 of different types in the successive layers or the adjacent contaminant resistant materials in the same layer of the contaminant resistant coating 4 may be separated from each other by a spacing of from about 1 micron to about 1 millimeter, for example and without limitation, in the pattern. Maintaining separation of the contaminant resistant materials of different type in the contaminant resistant coating 4 may optimize the contaminant resistant efficacy of each contaminant resistant material.

In typical application, the contaminant resistant coating 4 is applied to the substrate surface 3 of the substrate 2 typically as was heretofore described. The substrate surface 3 of the substrate 2 may be any surface which is to have contaminant resistant properties and may be such a surface in a commercial or military aircraft, rotorcraft or Unmanned Air Vehicle (UAV), for example and without limitation. In aerospace applications, the substrate 2 may be an air duct; lavatory; tray table; bulkhead; or insulation blanket, for example and without limitation. Accordingly, as shown in FIG. 2, each type of contaminant resistant material 8, 9, 10, 11 in the contaminant resistant coating 4 may kill or inactivate microbes 14 such as bacteria, fungi and/or viruses which fall within the range of microbes 14 acted upon by the contaminant resistant material and which contact the contaminant resistant coating 4.

Figure 4:
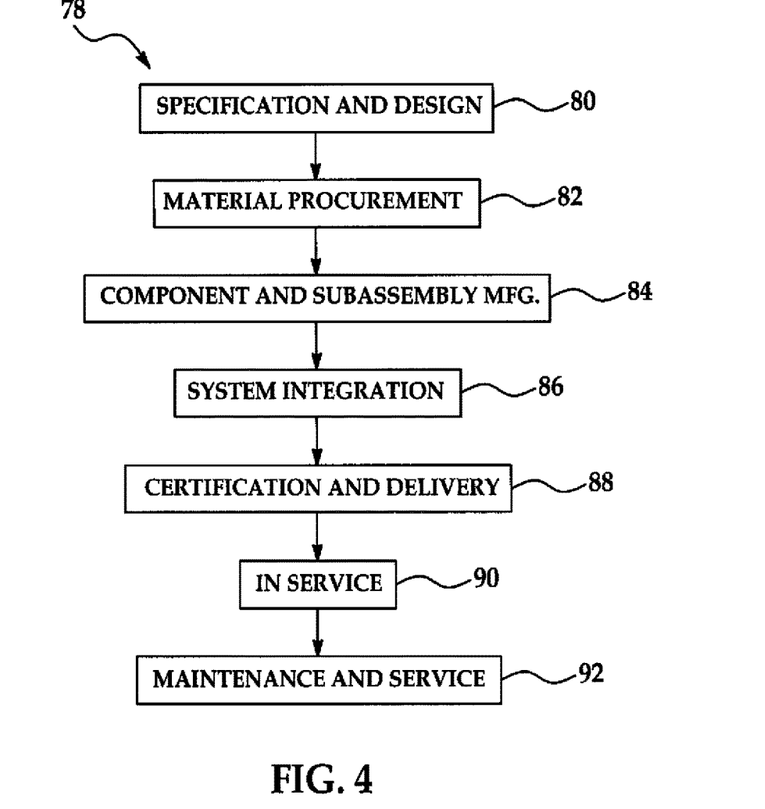
FIG. 4 is a flow diagram of an aircraft production and service methodology.
Figure 5:
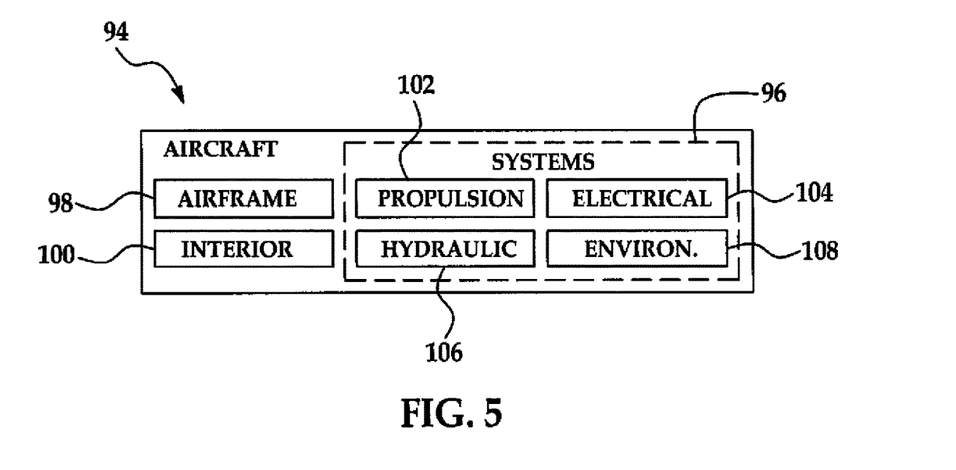
FIG. 5 is a block diagram of an aircraft.

Referring next to FIGS. 4 and 5, embodiments of the disclosure may be used in the context of an aircraft manufacturing and service method 78 as shown in FIG. 4 and an aircraft 94 as shown in FIG. 5. During pre-production, exemplary method 78 may include specification and design 80 of the aircraft 94 and material procurement 82. During production, component and subassembly manufacturing 84 and system integration 86 of the aircraft 94 takes place. Thereafter, the aircraft 94 may go through certification and delivery 88 in order to be placed in service 90. While in service by a customer, the aircraft 94 may be scheduled for routine maintenance and service 92 (which may also include modification, reconfiguration, refurbishment, and so on).

Each of the processes of method 78 may be performed or carried out by a system integrator, a third party, and/or an operator (e.g., a customer). For the purposes of this description, a system integrator may include without limitation any number of aircraft manufacturers and major-system subcontractors; a third party may include without limitation any number of vendors, subcontractors, and suppliers; and an operator may be an airline, leasing company, military entity, service organization, and so on.

As shown in FIG. 5, the aircraft 94 produced by exemplary method 78 may include an airframe 98 with a plurality of systems 96 and an interior 100. Examples of high-level systems 96 include one or more of a propulsion system 102, an electrical system 104, a hydraulic system 106, and an environmental system 108. Any number of other systems may be included. Although an aerospace example is shown, the principles of the disclosure may be applied to other industries, such as the automotive industry.

The apparatus embodied herein may be employed during any one or more of the stages of the production and service method 78. For example, components or subassemblies corresponding to production process 84 may be fabricated or manufactured in a manner similar to components or subassemblies produced while the aircraft 94 is in service. Also, one or more apparatus embodiments may be utilized during the production stages 84 and 86, for example, by substantially expediting assembly of or reducing the cost of an aircraft 94. Similarly, one or more apparatus embodiments may be utilized while the aircraft 94 is in service, for example and without limitation, to maintenance and service 92.

Figure 6:
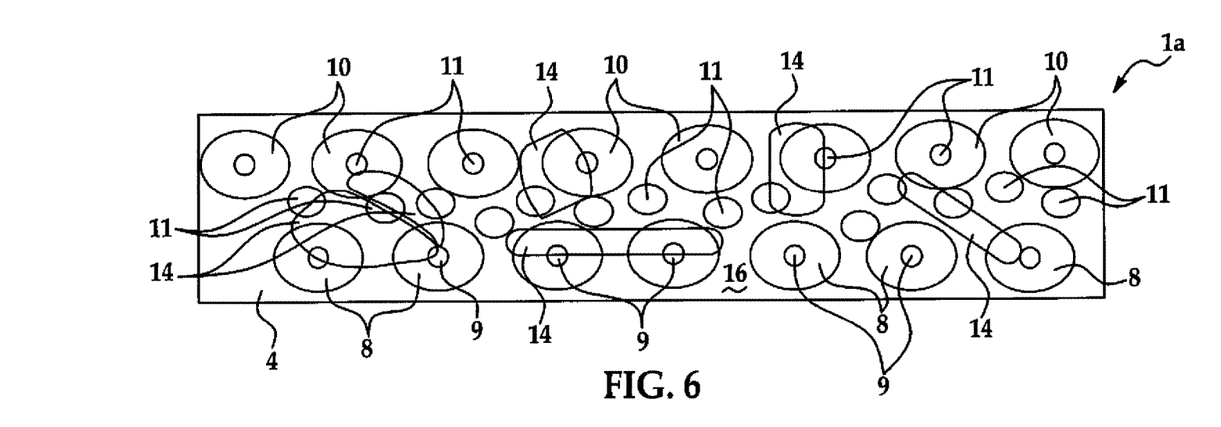
FIG. 6 is a top view of an illustrative embodiment of the contaminant resistant structure in which contaminant resistant materials are applied to a surface of a substrate in a coating according to geometrical parameters which optimize the contaminant resistant efficacy of the materials and a hydrophobic or oleophobic material is applied to the surface of the substrate.
Figure 7:
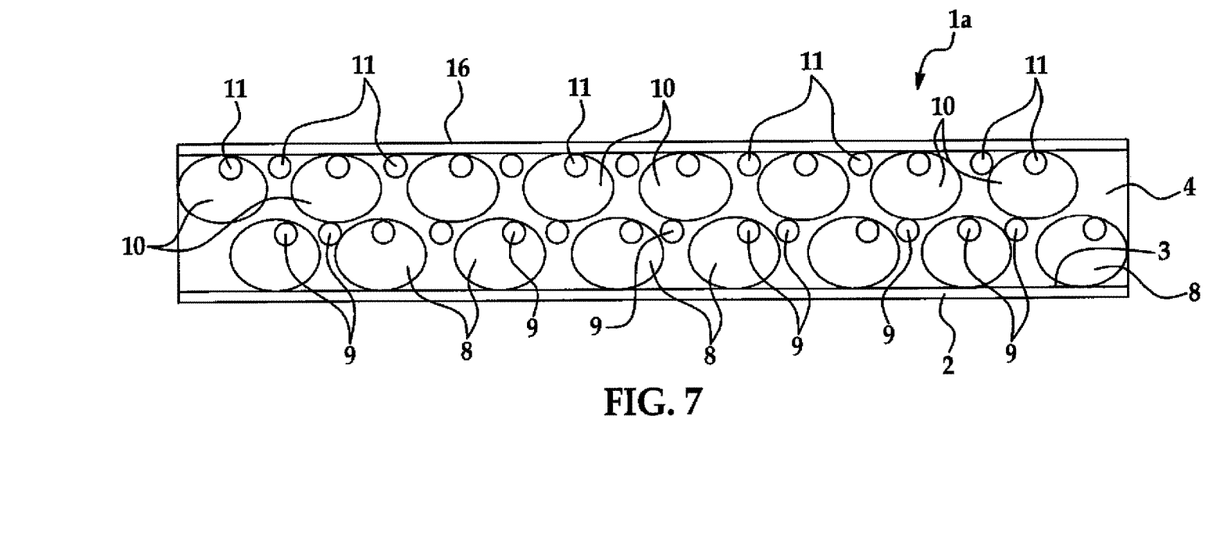
FIG. 7 is a side view of an illustrative embodiment of the contaminant resistant structure shown in FIG. 6.

Referring next to FIGS. 6 and 7, an alternative illustrative embodiment of the contaminant resistant structure is generally indicated by reference numeral 1a. The structure 1a may be similar in construction to the structure 1 which was heretofore described with respect to FIGS. 2 and 3. In the structure 1a, the substrate surface may be two-dimensional. A hydrophobic or oleophobic material 16 may be provided on at least a portion of the substrate surface 3 of the substrate 2. Accordingly, in application of the structure 1a, in the event that a liquid droplet (not shown) having microbes (not shown) contacts the substrate 2, the hydrophobic or oleophobic material 16 may repel the liquid droplet and the microbes such that the microbes contact the contaminant resistant material 8, 9, 10 or 11. The contaminant resistant material 8, 9, 10 and may kill, inactivate, denature or neutralize the microbes and render the substrate surface 3 of the substrate 2 sanitary.

Figure 8:
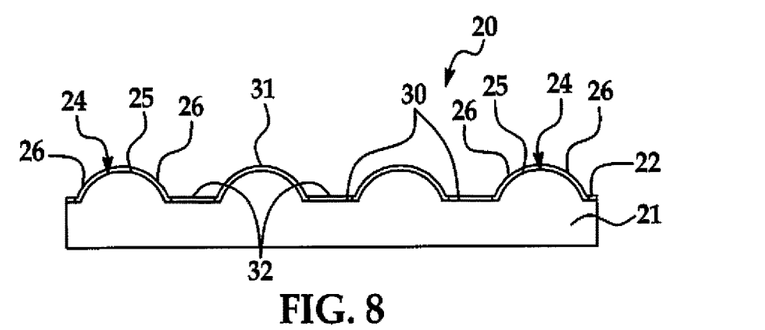
FIG. 8 is a cross-sectional view of an illustrative embodiment of a three-dimensional contaminant resistant structure, with a hydrophobic or oleophobic material provided on elevated surfaces and a contaminant resistant material provided on generally planar depressed surfaces of the structure.

Referring next to FIG. 8 of the drawings, an illustrative embodiment of a three-dimensional contaminant resistant structure, hereinafter structure, is generally indicated by reference numeral 20. The structure 20 may include a substrate 21 having a substrate surface 22. In some embodiments, contaminant resistant agents (not shown) may be embedded or otherwise provided internally in the substrate 21 according to the knowledge of those skilled in the art. The substrate 21 of the structure 20 may be any desired material the substrate surface 22 of which is to have contaminant resistant properties, including but not limited to plastic; metal; wood; glass; or fabric. Elevated surfaces 24 may be provided on the substrate surface 22 of the substrate 21. Depressed surfaces 30, each of which may be generally planar, may extend between the elevated surfaces 24. Each elevated surface 24 may have a top surface portion 25 and a side surface portion 26 which extends from the top surface portion 25 to the depressed surfaces 30. In some embodiments, the top surface portion 25 of each elevated surface 24 may be generally convex, as shown. In other embodiments, the top surface portion 25 may have alternative configurations. The elevated surfaces 24 may be formed on the substrate surface 22 of the substrate 21 using any suitable technique known to those skilled in the art. Techniques which are suitable for forming the elevated surfaces 24 on the substrate surface 22 include deposition techniques such as direct writing, inkjet deposition, stamping, spraying and dipping, for example and without limitation. Additionally or alternatively, the elevated surfaces 24 may be provided on the substrate surface 22 using techniques such as molding, embossing, stamping, machining, milling and/or drilling, for example and without limitation. The elevated surfaces 24 may be provided on the substrate surface 3 of the substrate 2 in any size and configuration and may be fabricated at the macro-scale, meso-scale, micro-scale or nano-scale level depending on the desired application of the structure 20.

A hydrophobic or oleophobic material 31 may be provided on each elevated surface 24 of the structure 20. In some embodiments, the hydrophobic or oleophobic material 31 may be confined to the top surface portion 25 of each elevated surface 24. In other embodiments, the hydrophobic or oleophobic material 31 may be confined to the side surface portion 26 of each elevated surface 24. In still other embodiments, the hydrophobic or oleophobic material 31 may be provided on the top surface portion 25 and the side surface portion 26 of each elevated surface 24.

A contaminant resistant material 32 may be provided on the depressed surfaces 30 of the structure 20. The contaminant resistant material 32 may be any type of material which is effective in killing microbes such as fungi or bacteria and/or killing, inactivating or denaturing viruses, weaponized biological agents and/or chemical agents, for example and without limitation. The hydrophobic or oleophobic material 31 and the contaminant resistant material 32 may be deposited on the elevated surfaces 24 and the depressed surfaces 30 using dipping, spraying and/or any other suitable deposition technique which is known to those skilled in the art.

The structure 20 may be used in any application in which it is desired to kill microbes such as fungi and bacteria and/or kill, inactivate, denature or neutralize viruses, weaponized biological agents and/or chemical agents which may be present in liquid droplets, for example and without limitation, that contact the structure 20. In some applications, the structure 1 may be provided on the interior surfaces of an aircraft (not shown). In some applications, the elevated surfaces 24 may function as wear pads on the substrate 21 and may offer wear protection to functionalities such as coatings, for example and without limitation, located at the depressed surfaces 30. In the event that a liquid droplet (not shown) which contains a microbe or biological agent (not shown) directly contacts a depressed surface 30, the microbe or biological agent may contact the contaminant resistant material 32, killing and/or denaturing or inactivating the microbe or biological agent. In the event that a liquid droplet which contains a microbe or biological agent contacts the hydrophobic or oleophobic material 31 provided on each elevated surface 24, the hydrophobic nature of the hydrophobic or oleophobic material 31 may repel the liquid droplet from the elevated surface 24 to the depressed surfaces 30 on the substrate 2. In some applications, the liquid droplet may move from the top surface portion 25 of the elevated surface 24 to the depressed surfaces 30 via gravity, capillary action and/or micro fluidic channel or channels, for example and without limitation. The microbes or biological agent in the liquid droplet may contact the contaminant resistant material 32 on the depressed surfaces 30, thereby killing, denaturing or inactivating the microbe or biological agent. Therefore, the contaminant resistant material 32 may maintain the substrate surface 22 of the substrate 21 in a sanitary condition. In some applications, oil, lubricating fluids or machining fluids (not shown) may be repelled by the hydrophobic or oleophobic material 31 and therefore, may flow from the top surface portion 25 and along the side surface portion 26 of each elevated surface 24 to the depressed surfaces 30.

Figure 9:
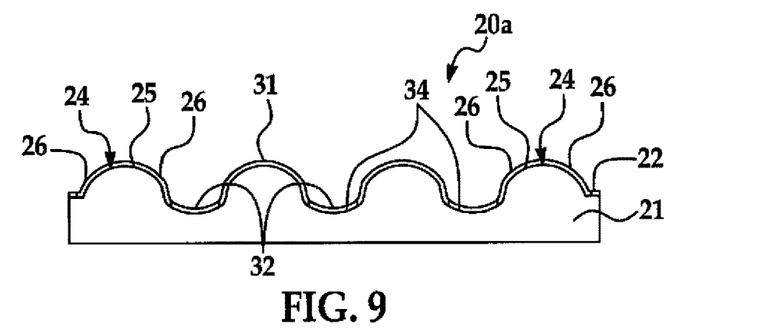
FIG. 9 is a cross-sectional view of an alternative illustrative embodiment of a three-dimensional contaminant resistant structure, with a hydrophobic or oleophobic material provided on elevated surfaces and a contaminant resistant material provided on generally concave depressed surfaces of the structure.

An alternative illustrative embodiment of the structure is generally indicated by reference numeral 20a in FIG. 9. In the structure 20a, generally concave or depressed surfaces 34 may extend between the elevated surfaces 24. The contaminant resistant material 32 may be provided on the generally concave or depressed surfaces 34. Application of the structure 20a may be as was heretofore described with respect to the structure 20 in FIG. 8.

Figure 12:
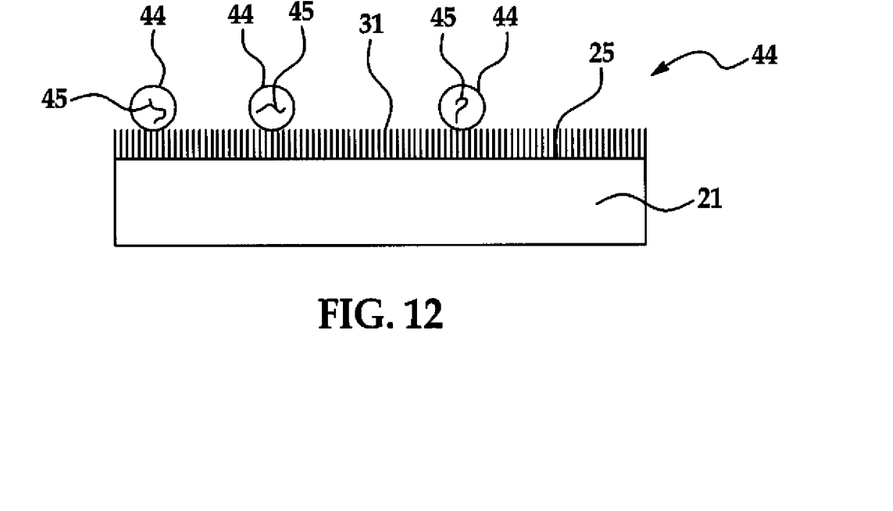
FIG. 12 is a cross-sectional view of an illustrative embodiment of a three-dimensional contaminant resistant structure, with a hydrophobic or oleophobic material provided on a surface of a substrate and liquid droplets containing a microbe repelled by the hydrophobic or oleophobic material.
Figure 13:
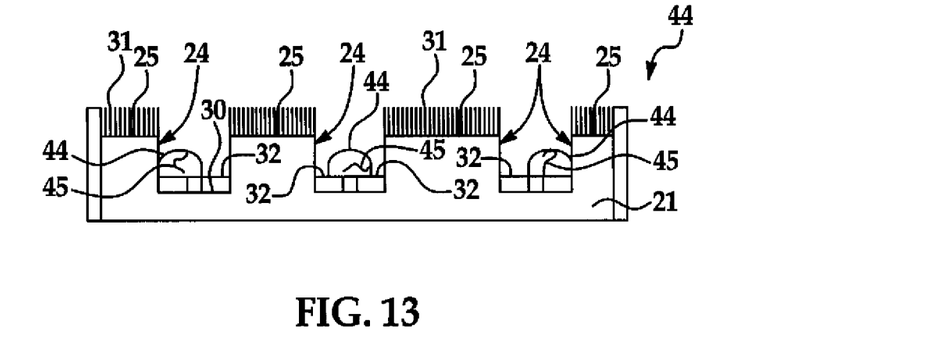
FIG. 13 is a cross-sectional view of an illustrative embodiment of a three-dimensional contaminant resistant structure, with a hydrophobic or oleophobic material provided on elevated surfaces of a substrate and a contaminant resistant material provided on generally planar depressed surfaces of the substrate and liquid droplets containing a microbe on the contaminant resistant material on the depressed surfaces.

Another alternative illustrative embodiment of the structure 44 is shown in FIGS. 12 and 13. In the structure 44, the top surface portion 25 of each elevated surface 24 may be generally planar. The side surface portions 26 of each elevated surface 24 may be disposed in generally perpendicular relationship with respect to the top surface portion 25. In FIG. 12, multiple liquid droplets 44, each of which contains microbes or biological agents 45, are shown on the hydrophobic or oleophobic material 31 which is provided on the top surface portion 25 of each elevated surface 24. As shown in FIG. 13, the hydrophobic or oleophobic material 31 may repel the liquid droplets 44 from the elevated surfaces 24 onto the depressed surfaces 30, where the contaminant resistant material 32 may contact and kill or inactivate, denature or neutralize the microbes or biological agents 45 contained in the liquid droplets 44. In some applications, the liquid droplets 44 may move from the top surface portion 25 of the elevated surface 24 to the depressed surfaces 30 via gravity and/or capillary action.

Figure 10:
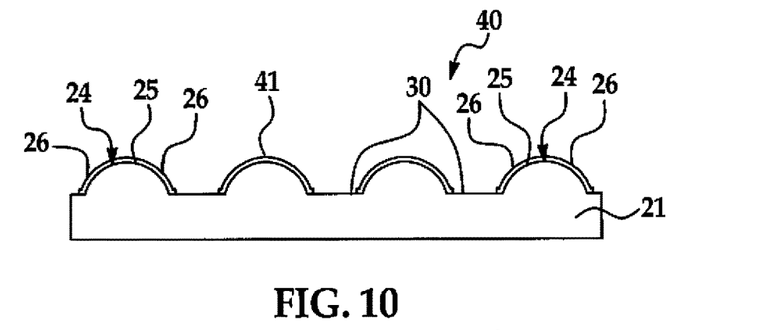
FIG. 10 is a cross-sectional view of another alternative illustrative embodiment of a three-dimensional contaminant resistant structure, with a hydrophilic or oleophilic material provided on elevated surfaces of the structure and exposed generally planar depressed surfaces between the elevated surfaces.

Referring next to FIG. 10, an alternative illustrative embodiment of a three-dimensional contaminant resistant structure is generally indicated by reference numeral 40. The structure 40 may include a substrate 21 having a substrate surface 22. Multiple elevated surfaces and depressed surfaces 30 may be provided on the substrate surface 22 as was heretofore described with respect to the structure 20 in FIG. 8. A hydrophilic or oleophilic material 41 may be provided on each elevated surface 24. In some embodiments, the hydrophilic or oleophilic material 41 may be confined to the top surface portion 25 of each elevated surface 24. In other embodiments, the hydrophilic or oleophilc material 41 may be confined to the side surface portion 26 of each elevated surface 24. In still other embodiments, the hydrophilic or oleophilic material 41 may be provided on the top surface portion 25 and the side surface portion 26 of each elevated surface 24.

Application of the structure 40 may be as was heretofore described with respect to the structure 20 in FIG. 8. Accordingly, in the event that a liquid droplet (not shown) which contains microbes (not shown) contacts an elevated surface 24, the hydrophilic or oleophilic material may confine the droplet and the microbes contained therein to the top surface portion 25 and/or the side surface portion 26 of each elevated surface 24. In some embodiments, the depressed surfaces 30 may be reserved for functionalities other than the killing, denaturing or neutralizing of microbes or biological agents since the microbes or biological agents may be immobilized on the elevated surfaces 24.

Figure 11:
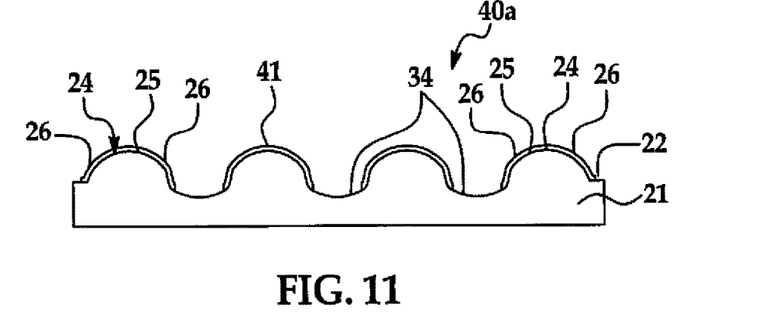
FIG. 11 is a cross-sectional view of another alternative illustrative embodiment of a three-dimensional contaminant resistant structure, with a hydrophilic or oleophilic material provided on elevated surfaces of the structure and exposed generally concave depressed surfaces between the elevated surfaces.

An alternative illustrative embodiment of the structure is generally indicated by reference numeral 40a in FIG. 11. In the structure 40a, generally concave or depressed surfaces 34 may extend between the elevated surfaces 24. Application of the structure 40a may be as was heretofore described with respect to the structure 20 in FIG. 8.

Figure 14:
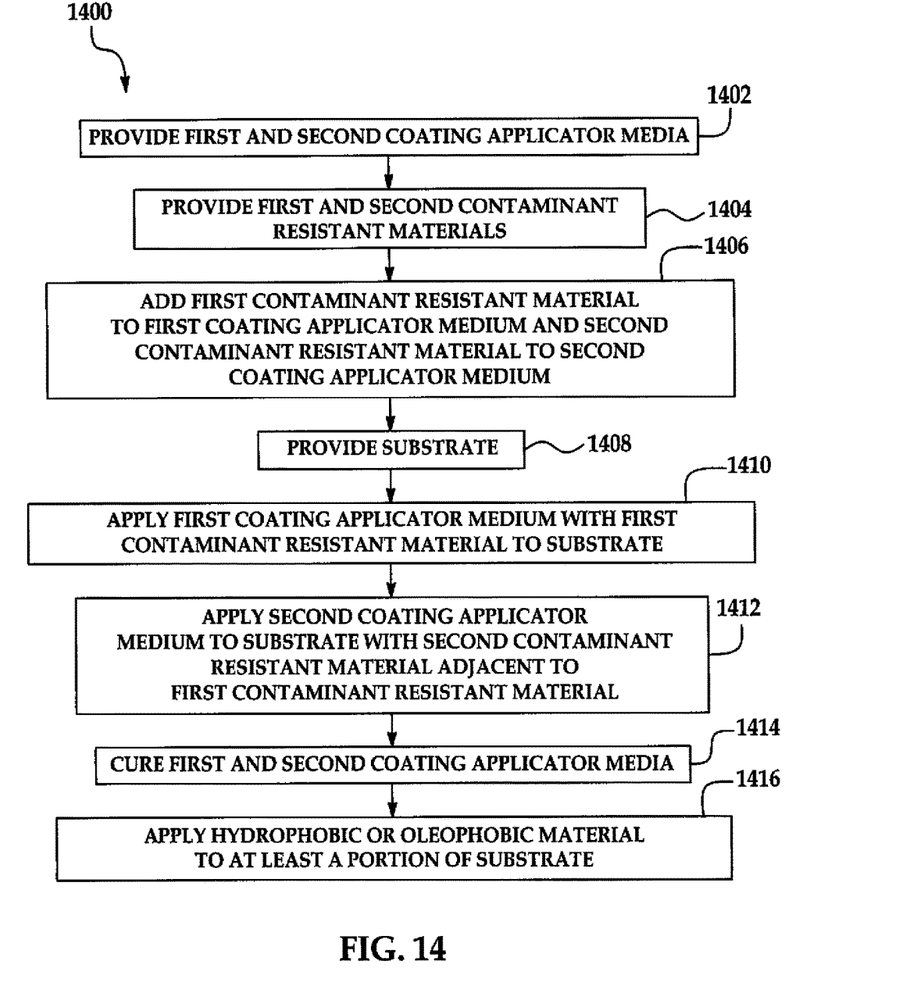
FIG. 14 is a flow diagram of an illustrative method which is suitable for fabrication of the contaminant resistant structure shown in FIGS. 6 and 7.

Referring next to FIG. 14, flow diagram 1400 of an illustrative method which is suitable for fabrication of the contaminant resistant structure shown in FIGS. 6 and 7 is shown. In block 1402, first and second coating applicator media may be provided. In bock 1404, first and second contaminant resistant materials may be provided. In block 1406, the first contaminant resistant material may be added to the first coating applicator medium and the second contaminant resistant material may be added to the second coating applicator medium. In block 1408, a substrate may be provided. In block 1410, the first coating applicator medium with the first contaminant resistant material may be added to the substrate. In block 1412, the second coating applicator medium may be added to the substrate with the second contaminant resistant material adjacent to the first contaminant resistant material. In block 1414, the first and second coating applicator media may be cured. In block 1416, a hydrophobic or oleophobic material may be applied to at least a portion of the substrate.

Figure 15:
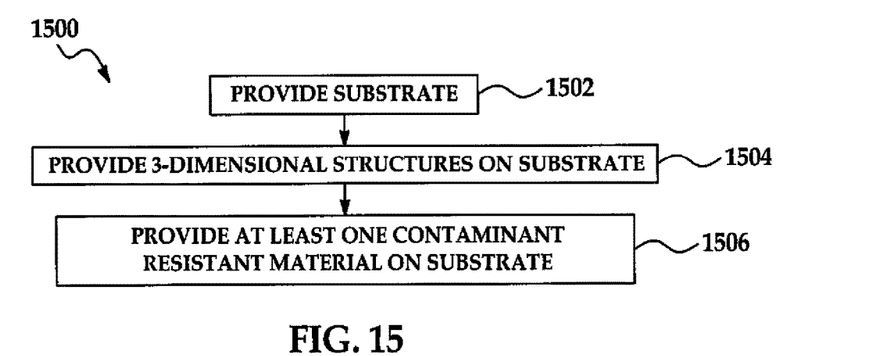
FIG. 15 is a flow diagram of an illustrative method which is suitable for fabrication of the three-dimensional contaminant resistant structures shown in FIGS. 8, 9, 12 and 13.

Referring next to FIG. 15, a flow diagram 1500 of an illustrative method which is suitable for fabrication of the three-dimensional contaminant resistant structures shown in FIGS. 8, 9, 12 and 13 is shown. In block 1502, a substrate may be provided. In block 1504, three-dimensional structures may be provided on the substrate. In some embodiments, the three-dimensional structures may include elevated surfaces and depressed surfaces extending between the elevated surfaces. In block 1506, at least one contaminant resistant material may be provided on the substrate. In some embodiments, the contaminant resistant material may be provided on the elevated surfaces.

Figure 16:
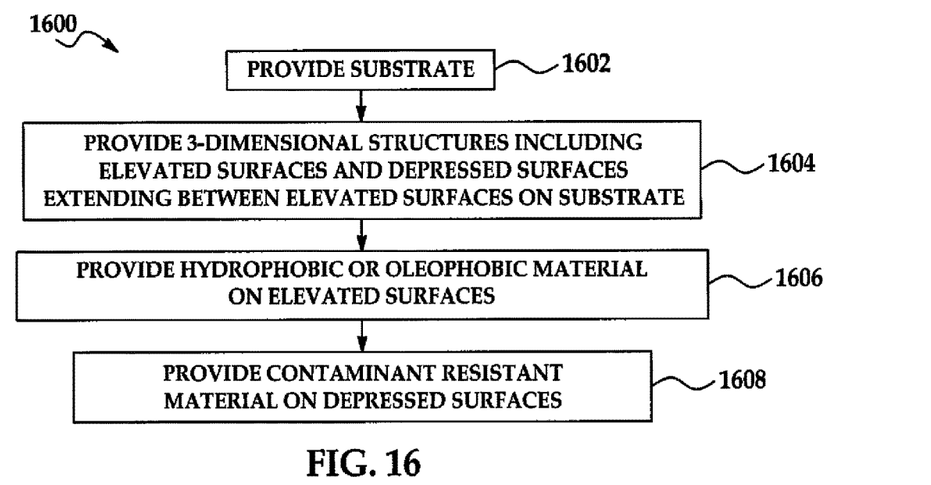
FIG. 16 is a flow diagram of an illustrative method which is suitable for fabrication of the three-dimensional contaminant resistant structures shown in FIGS. 8, 9, 12 and 13.

Referring next to FIG. 16, a flow diagram 1600 of an illustrative method which is suitable for fabrication of the three-dimensional contaminant resistant structures shown in FIGS. 8, 9, 12 and 13 is shown. In block 1602, a substrate may be provided. In block 1604, three-dimensional structures including elevated surfaces and depressed surfaces extending between the elevated surfaces may be provided on the substrate. In block 1606, hydrophobic or oleophobic material may be provided on the elevated surfaces. In some embodiments, hydrophobic or oleophobic material may be provided on at least one of a top surface portion and a side surface portion of each elevated surface. In block 1608, contaminant resistant material may be provided on the depressed surfaces between the elevated surfaces.

Figure 17:
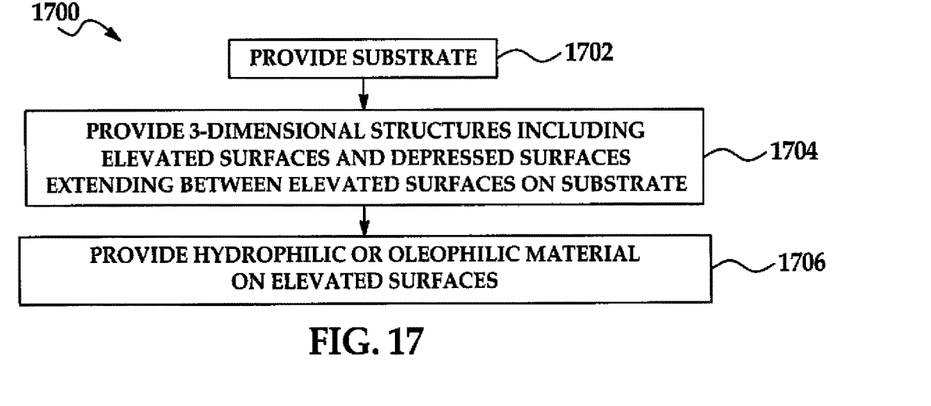
FIG. 17 is a flow diagram of an illustrative method which is suitable for fabrication of the three-dimensional contaminant resistant structures shown in FIGS. 10 and 11.

Referring next to FIG. 17, a flow diagram 1700 of an illustrative method which is suitable for fabrication of the three-dimensional contaminant resistant structures shown in FIGS. 10 and 11 is shown. In block 1702, a substrate may be provided. In block 1704, three-dimensional structures including elevated surfaces and depressed surfaces extending between the elevated surfaces may be provided on the substrate. In block 1706, hydrophilic or oleophilic material may be provided on the elevated surfaces. In some embodiments, hydrophilic or oleophilic material may be provided on at least one of a top surface portion and a side surface portion of each elevated surface.

Although the embodiments of this disclosure have been described with respect to certain exemplary embodiments, it is to be understood that the specific embodiments are for purposes of illustration and not limitation, as other variations will occur to those of skill in the art.

What is claimed is:

1. A structure, comprising:
   spaced protrusions between which recesses are defined;
   a biocidal material disposed in the recesses; and
   a relatively hydrophobic or oleophobic material compared to the biocidal material disposed on the protrusions, wherein the hydrophobic or oleophobic material is confined to a portion of each of the protrusions.

2. The structure of claim 1, wherein the protrusions comprise peak heights of less than about 3 microns.

3. The structure of claim 1, wherein the protrusions comprise peak heights of greater than about 3 microns.

4. The structure of claim 1, wherein the recesses comprise generally planar depressed surfaces.

5. The structure of claim 1, wherein the recesses comprise generally concave depressed surfaces.

6. The structure of claim 1, wherein the recesses are spaced apart about 1 micron to about 1 millimeter.

7. The structure of claim 1, further including channels disposed between the protrusions and the recesses.

8. A structure comprising:
   a substrate surface having peaks comprising heights of greater than about 3 microns;
   depressions disposed between the peaks;
   a biocidal material disposed in the depressions; and
   an additional material disposed on the peaks, the additional material having an increased hydrophobic property or an increased oleophobic property relative to the biocidal material, wherein the additional material is confined to a portion of each of the peaks.

9. The structure of claim 8, wherein the depressions comprise generally planar depressed surfaces.

10. The structure of claim 8, wherein the depressions comprise generally concave depressed surfaces.

11. A structure comprising:
    a substrate surface having peaks comprising heights of greater than about 3 microns;
    depressions disposed between the peaks;
    a biocidal material disposed in the depressions; and
    an additional material disposed on the peaks, the additional material having an increased hydrophilic property or an increased oleophilic property relative to the biocidal material, wherein the additional material is confined to a portion of each of the peaks.

12. A structure, comprising:
    a substrate having a substrate surface including elevated surfaces and depressions extending between the elevated surfaces;
    a biocidal material disposed in the depressions; and
    a relatively hydrophobic or oleophobic material compared to the biocidal material disposed on the elevated surfaces, wherein the hydrophobic or oleophobic material is confined to a portion of each of the elevated surfaces.

13. A structure, comprising:
    a substrate having convex portions and depressions disposed between the convex portions;

a biocidal material disposed in the depressions; and
a relatively hydrophobic or oleophobic material compared to the biocidal material disposed on the convex portions, the hydrophobic or oleophobic material confined to a portion of each of the convex portions.

\* \* \* \* \*